US 8,986,981 B2

(12) United States Patent
Toumazou et al.

(10) Patent No.: US 8,986,981 B2
(45) Date of Patent: Mar. 24, 2015

(54) DETECTION OF METHYLATED DNA

(75) Inventors: Christofer Toumazou, London (GB); Melpomeni Kalofonou, London (GB)

(73) Assignee: Oncu Limited, Tortola (VG)

( * ) Notice: Subject to any disclaimer, the term of this patent is extended or adjusted under 35 U.S.C. 154(b) by 0 days.

(21) Appl. No.: 13/634,548

(22) PCT Filed: Mar. 14, 2011

(86) PCT No.: PCT/GB2011/050501
§ 371 (c)(1),
(2), (4) Date: Oct. 1, 2012

(87) PCT Pub. No.: WO2011/110873
PCT Pub. Date: Sep. 15, 2011

(65) Prior Publication Data
US 2013/0034851 A1    Feb. 7, 2013

(30) Foreign Application Priority Data

Mar. 12, 2010    (GB) .................................. 1004147.3

(51) Int. Cl.
*C12M 1/34* (2006.01)
*C12Q 1/68* (2006.01)
(Continued)

(52) U.S. Cl.
CPC .......... *G01N 27/4145* (2013.01); *C12Q 1/6825* (2013.01); *C12Q 1/6858* (2013.01); *C12Q 1/6869* (2013.01)
USPC ......... 435/287.2; 435/6.1; 204/416; 257/253; 422/82.01; 422/82.03; 438/10

(58) Field of Classification Search
CPC .. C12Q 1/6825; C12Q 1/6858; C12Q 1/6839; G01N 27/4145

USPC ................. 435/6.1, 287.2; 257/253; 204/416; 422/82.03, 82.04; 438/10
See application file for complete search history.

(56) References Cited

U.S. PATENT DOCUMENTS 7,686,929 B2    3/2010    Toumazou et al.
7,888,015 B2    2/2011    Toumazou et al.
(Continued)

FOREIGN PATENT DOCUMENTS

WO    2008/076406    6/2008
WO    2008/107014    9/2008
(Continued)

OTHER PUBLICATIONS

Garner et al, A Multichannel DNA SoC for Rapid Point-of-Care Gene Detection, presented at 2010 IEEE International Solid-State Circuits Conference, session 27.4, Feb. 10, 2010, pp. 1-3.*
(Continued)

*Primary Examiner* — Narayan Bhat
(74) *Attorney, Agent, or Firm* — Nixon & Vanderhye PC

(57) ABSTRACT

The use of ion sensitive field effect transistor (ISFET) to detect methylated nucleotides in a DNA sample is described. A method of detecting methylated nucleotides in a DNA sample may include the steps of treating a sample of DNA with a reagent which discriminates between methylated and non-methylated nucleotides to provide treated DNA, amplifying the treated DNA and optionally sequencing the amplified DNA. An ISFET is used to monitor the addition of one or more dNTPs in the strand extension reactions during the amplification and/or sequencing step. Suitable apparatus is also provided.

19 Claims, 14 Drawing Sheets

(51) Int. Cl.
*G01N 27/403* (2006.01)
*G01N 27/00* (2006.01)
*G01N 27/30* (2006.01)
*H01L 21/00* (2006.01)
*G01N 27/414* (2006.01)

(56) References Cited

U.S. PATENT DOCUMENTS

| | | | |
|---|---|---|---|
| 8,114,591 | B2 | 2/2012 | Toumazou et al. |
| 2002/0197639 | A1* | 12/2002 | Shia et al. ............ 435/6 |
| 2004/0134798 | A1 | 7/2004 | Toumazou et al. |
| 2008/0032295 | A1 | 2/2008 | Toumazou et al. |
| 2009/0127589 | A1 | 5/2009 | Rothberg et al. |
| 2010/0151479 | A1 | 6/2010 | Toumazou et al. |
| 2010/0188073 | A1 | 7/2010 | Rothberg et al. |
| 2010/0197507 | A1 | 8/2010 | Rothberg et al. |
| 2010/0255595 | A1 | 10/2010 | Toumazou et al. |
| 2010/0260745 | A1 | 10/2010 | Zhou et al. |
| 2010/0292348 | A1 | 11/2010 | Zhou et al. |
| 2012/0175252 | A1 | 7/2012 | Toumazou et al. |
| 2013/0034851 | A1 | 2/2013 | Toumazou et al. |

FOREIGN PATENT DOCUMENTS

| | | |
|---|---|---|
| WO | 2009/046110 | 4/2009 |
| WO | 2010/028288 | 3/2010 |

OTHER PUBLICATIONS

Kalofonou et al, An ISFET based translinear sensor for DNA methylation detection, 2012, Sensors and Actuators B, 161, 156-162.*

International Search Report for PCT/GB2011/050501, three pages, mailed Jun. 7, 2011.

Maki et al. "Nanowire-transistor based ultra-sensitive DNA methylation detection" *Biosensors and Bioelectronics*, vol. 23, No. 6, pp. 780-787 (Dec. 2007).

* cited by examiner

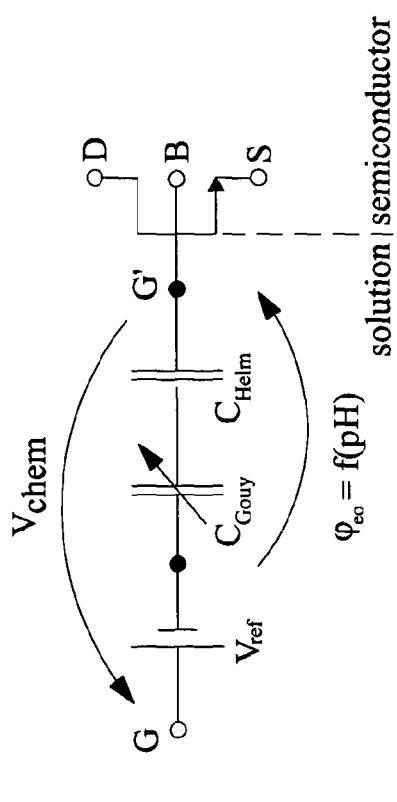
Figure 2a: ISFET macromodel
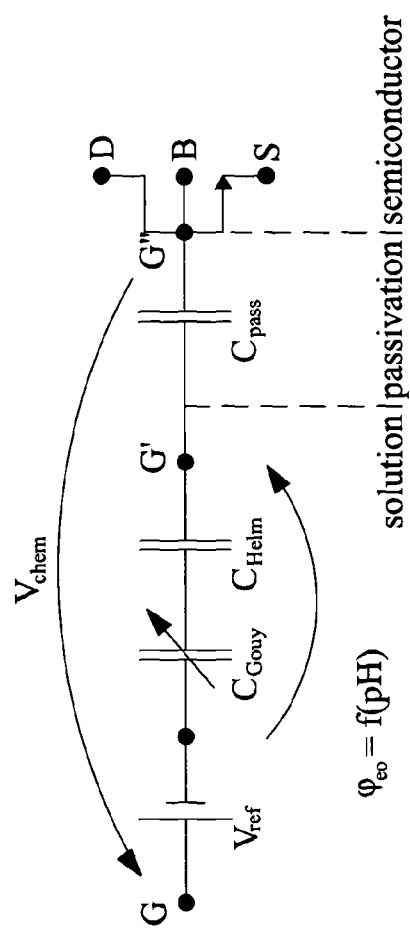
Figure 2b: CMOS ISFET macromodel

DETECTION OF METHYLATED DNA

This application is the U.S. national phase of International Application No. PCT/GB2011/050501, filed 14 Mar. 2011, which designated the U.S., claims priority to United Kingdom Application No. 1004147.3, filed 12 Mar. 2010, the entire contents of each of which are hereby incorporated by reference.

FIELD OF THE INVENTION

The present invention relates to a sensing apparatus and method, and particularly to a sensing apparatus and method suitable for detecting methylated DNA.

BACKGROUND

In the chemical sciences, methylation denotes the addition of a methyl group to a substrate or the substitution of an atom or group by a methyl group. Methylation is a form of alkylation with specifically a methyl group, rather than a larger carbon chain, replacing a hydrogen atom. These terms are commonly used in chemistry, biochemistry, soil science, and the biological sciences.

In biological systems, methylation is catalyzed by enzymes; such methylation can be involved in modification of heavy metals, regulation of gene expression, regulation of protein function, and RNA metabolism. Methylation of heavy metals can also occur outside of biological systems. Chemical methylation of tissue samples is also one method for reducing certain histological staining artefacts.

DNA methylation in vertebrates typically occurs at CpG sites (cytosine-phosphate-guanine sites; that is, where a cytosine is directly followed by a guanine in the DNA sequence); this methylation results in the conversion of the cytosine to 5-methylcytosine. The formation of Me-CpG is catalyzed by the enzyme DNA methyltransferase. The bulk of mammalian DNA has about 40% of CpG sites methylated but there are certain areas, known as CpG islands which are GC rich (made up of about 65% CG residues) where none are methylated. These are associated with the promoters of 56% of mammalian genes, including all ubiquitously expressed genes. 1-2% of the human genome are CpG clusters and there is an inverse relationship between CpG methylation and transcriptional activity.

DNA methylation involves the addition of a methyl group to the 5 position of cytosine pyrimidine ring or the number 6 nitrogen of the adenine purine ring (cytosine and adenine are two of the four bases of DNA). This modification can be inherited through cell division. DNA methylation is typically removed during zygote formation and re-established through successive cell divisions during development. DNA methylation is a crucial part of normal organism development and cellular differentiation in higher organisms. DNA methylation stably alters the gene expression pattern in cells such that cells can "remember where they have been"; in other words, cells programmed to be pancreatic islets during embryonic development remain pancreatic islets through out the life of the organism without continuing signals telling them that they need to remain islets. In addition, DNA methylation suppresses the expression of viral genes and other deleterious elements which have been incorporated into the genome of the host over time. DNA methylation also forms the basis of chromatin structure, which enables cells to form the myriad characteristics necessary for multicellular life from a single immutable sequence of DNA. DNA methylation also plays a crucial role in the development of nearly all types of cancer.

DNA methylation involves the addition of a methyl group to DNA—for example, to the number 5 carbon of the cytosine pyrimidine ring—in this case with the specific effect of reducing gene expression. In adult somatic tissues, DNA methylation typically occurs in a CpG dinucleotide context; non-CpG methylation is prevalent in embryonic stem cells.

Bisulfite sequencing is the use of bisulfite treatment of DNA to determine its pattern of methylation. DNA methylation was the first discovered epigenetic mark, and remains the most studied. It is also implicated in repression of transcriptional activity.

Treatment of DNA with bisulfite converts cytosine residues to uracil, but leaves 5-methylcytosine residues unaffected. Thus, bisulfite treatment introduces specific changes in the DNA sequence that depend on the methylation status of individual cytosine residues, yielding single-nucleotide resolution information about the methylation status of a segment of DNA. Various analyses can be performed on the altered sequence to retrieve this information. The objective of this analysis is therefore reduced to differentiating between single nucleotide polymorphisms (cytosines and thymines) resulting from bisulfite conversion.

Sequencing can be done by pyrosequencing, which differs from Sanger sequencing, relying on the detection of pyrophosphate release on nucleotide incorporation, rather than chain termination with dideoxynucleotides.

The Illumina Methylation Assay using the Infinium II platform uses "BeadChip" technology to generate a comprehensive genome wide profiling of human DNA methylation, similar to bisulfite sequencing and pyrosequencing. According to Staaf et al. (2008), "the Infinium II assay seemed to have dye intensity biases between the two channels used in fluorescence detection. Furthermore, this bias was not eliminated even after the data had gone through normalization algorithms used in the BeadStudio software".

The samples used for the analysis of DNA methylation biomarkers usually contain high concentrations of background DNA from the tumour. However, tumour-derived DNA is difficult to be detected because it is often present in very low concentrations and can be contaminated substantially with DNA from healthy cells. Thus, methods with sensitive detection capabilities of single copies of methylated DNA in a high amount of unmethylated background DNA are often needed to identify aberrantly methylated tumour-derived DNA in body fluids.

The combination of different types of pre-treatment of sample DNA followed by different analytical steps has resulted in a plethora of techniques for determining DNA methylation patterns and profiles.

In particular, the methods of methylome analysis are divided into 3 groups: restriction enzyme based, Chromatin immunoprecipitation based (ChIP) or affinity based and bisulfite conversion (gene based). Restriction enzyme based methods use methylation-sensitive restriction enzymes for small/large scale DNA methylation analysis by combining the use of methylation-sensitive restriction enzymes with experimental approaches (RLGS, DMH etc.) for global methylation analysis, applied to any genome without knowing the DNA sequence. However, large amounts of genomic DNA are required, making the method unsuitable for the analysis of samples when small amount of DNA is recovered. On the other hand, ChIP based methods are useful for the identification of differential methylated regions in tumours through the precipitation of a protein antigen out of a solution by using an antibody directed against the protein. These methods are protein based, applied extensively in cancer research.

Despite several advantages, protein based methods are limited in detecting methyl ($CH_3$) groups in defined sites, with limitations on the data obtained by the frequency of the restriction enzyme recognition sequence, becoming complex when extra amplification is needed after the antibodies attachment.

MSP is known for its high analytical sensitivity, which however can be influenced by the primer design and the number of PCR cycles. Thus, there is a risk of false-positive results arising, which is claimed to be one of the most significant problems when using the methylation technology in cancer early recognition, so increasing the specificity of methylation detection represents an important step in the development of adequate early recognition tests.

The present inventor has appreciated that existing methods have high cost requiring means to detect the fluorescence and are generally not compatible with standard high-volume manufacturing techniques like CMOS processes.

SUMMARY OF THE INVENTION

According to a first aspect of the present invention there is provided a use of ion sensitive field effect transistor (ISFET) to detect methylated nucleotides in a DNA sample.

According to a second aspect of the present invention there is provided a method of detecting methylated nucleotides in a DNA sample, comprising the steps of:
treatment of a sample of DNA with a reagent which discriminates between methylated and non-methylated nucleotides to provide treated DNA;
amplification of the treated DNA; and
optionally, sequencing of the amplified DNA;
wherein an ISFET monitors addition of one or more dNTPs to DNA strands during the strand extension reactions of the amplification and/or sequencing step.

During amplification and sequencing-by-synthesis, ions are released or consumed. For example, hydrogen ions are released when nucleotides are incorporated in the strand extension reactions. These ions can be detected by an ISFET to cause a change in the electrical signal output.

The reagent may be an antibody which selectively binds to the methyl group of methylated nucleotides in the DNA sample. The sample may then be subjected to immunoprecipitation, thereby separating the antibody-bound DNA fragments (i.e. methylated fragments) from non-antibody bound fragments (i.e. non-methylated fragments).

Prior to treatment with the reagent, the DNA sample may be subjected to one or more additional processes. The DNA may be purified, or processed so as to break up the DNA strands into smaller fragments. For example, the DNA may be subjected to sonication or restriction enzyme digestion.

The reagent may react selectively with methylated or non-methylated nucleotides. In an embodiment, the reagent comprises bisulfite, which converts only non-methylated cytosines in the DNA sample to uracil, leaving the methylated cytosines unchanged. In a particular embodiment, the reagent is sodium bisulfite.

Amplification of the DNA may be carried out using PCR (the Polymerase Chain Reaction) or Isothermal amplification. Methylated nucleotides may be detected by performing quantitative PCR on the treated DNA strands.

Where the DNA is treated with bisulfite (the $HSO_3^-$ ion, for example, sodium bisulfite, $NaHSO_3$.), PCR may be carried out using methylation-specific primers. Methylation-specific primers incorporate guanine at locations corresponding to methylated cytosine in the original DNA sample. Since methylated cytosine is not converted to uracil by the bisulfite, the guanine nucleotides will be complementary to the non-converted cytosines, allowing the primer to bind to the treated DNA, thereby enabling only treated DNA strands from the methylated samples to be amplified.

Alternatively, non-methylation-specific primers may be used, which enable only treated DNA strands from the unmethylated samples to be amplified. These primers incorporate adenine instead of guanine at locations corresponding to non-methylated cytosine in the original sample. Since non-methylated cytosine is converted to uracil by bisulfite, the adenine will be complementary to the uracil, allowing the primer to bind to the treated DNA and thereby enabling only treated DNA strands from non-methylated samples to be amplified.

In a particular embodiment, the method comprises the steps of:
treatment of a sample of DNA with bisulfite which converts unmethylated cytosines to uracil to provide treated DNA; and
PCR amplification of the treated DNA using methylation-specific or non-methylation specific primers;
wherein an ISFET monitors addition of dNTPs to strand extension reactions during PCR.

Conveniently, this method allows the detection of methylation in a DNA sample directly during the course of a PCR reaction, without requiring subsequent analysis (for example by sequencing) of the PCR products, although sequencing can also be performed, if required.

The invention also encompasses uses or methods of detecting methylated nucleotides in a DNA sample by providing a sample to be measured and treating the sample with a process whose operation discriminates between methylated nucleotides and non-methylated nucleotides. A direct or indirect result of the process is detected using an ion sensitive field effect transistor (ISFET).

The result may be a by-product of a chemical reaction.

A reaction will typically comprise several thousand molecules all undergoing the same reaction at the same time.

The reaction may be DNA synthesis, and the fluctuations of ionic charge indicate the insertion of di-deoxynucleotide triphosphates (ddNTP) and deoxynucleotide triphosphates (dNTP).

The type or quantity of by-product depends on the methylation of one or more nucleotides.

A sample of DNA to be checked may be treated with Bisulphite to change the methylated cytosine to uraciluracil.

The treated strands may undergo a process that creates DNA strands where the uracil, if present, has been replaced by thymine.

The treated strands may undergo amplification, for example PCR or Isothermal. During amplification many copies of the treated strands are made. These can be sequenced by many processes, during which process ions are released or consumed. For example, hydrogen ions may be released during the incorporation of a nucleotide into the strands during sequencing by synthesis. These ions can be detected by an ISFET to cause a change in the electrical signal output.

The methylated nucleotide may be detected by performing quantitative PCR on the treated strands. Methylation specific primers may be used which enable only treaded strands from the methylated samples to be amplified. Alternatively or separately, non-methylation specific primers may be used which enable only treaded strands from the unmethylated samples to be amplified.

The current method allows the detection of the methylation status of a few positions directly during the course of a PCR without requiring subsequent analysis of the products.

According to another aspect of the invention there is provided a method of determining the location of one or more methylated nucleotides in a DNA strand.

According to a further aspect of the invention there is provided a method of determining the quantity of methylated nucleotides in a DNA sample.

According to a further aspect of the invention there is provided an apparatus for detecting methylated DNA, said apparatus comprising an ISFET on a first substrate, and a second substrate having a microfludic chamber for bringing a DNA sample into contact with the ISFET. The apparatus may contain bisulphite.

The apparatus may further comprise a thermocycler for performing PCR.

The apparatus may comprise a single reaction chamber, or multiple reaction chambers. Each chamber may contain an ISFET. In a particular embodiment, 4 chambers are provided, each containing an ISFET. Each chamber may contain a different dNTP or a different primer or probe for use in a PCR reaction.

In an aspect of the invention, there is provided an apparatus for measuring DNA methylation, said apparatus comprising:
 a first Ion Sensitive Field Effect Transistor (ISFET) exposable to a first sample containing DNA;
 a second ISFET exposable to a second sample containing DNA; and
 a circuit providing an output signal, which output signal is derived from signals of the first and second ISFET.

The second sample may be a reference sample having a known amount of methylation.

The first sample is may be a methylated sample and may be compared to a second sample which may be an unmethylated sample The output signal may be a ratio of the signals of the first and second ISFET The apparatus may further comprise a plurality of first ISFETs, each ISFET exposable to samples looking at different methylation clusters.

The ISFETs may be biased to operate in the weak inversion region.

The ISFETs and circuit may be integrated on a substrate, the transistors of the ISFETs forming part of the circuit.

The signals of the ISFETs may be electrical currents and the output signal of the circuit may be a ratio of said electrical currents.

The output signal in above-mentioned apparatus may be compared to a threshold signal to indicate a potential diagnostic or therapeutic outcome associated with a comparative methylation value at the site of interest.

In any aspect of the invention, chain extension and hydrogen ion release may occur, resulting in discrete fluctuations in the electrical output and signal of the ISFET. This may be compared with a control, for example as described herein. For instance, the electrical output and signal of the ISFET may be compared with the absence of a target sequence complimentary to the probe. The electrical output signal of the ISFET is monitored after addition of dNTPs.

BRIEF DESCRIPTION OF THE DRAWINGS

Specific embodiments of the invention will now be described by way of example only with reference to the accompanying figures, in which:

FIG. 2a shows an IFSET macromodel;

FIG. 2b shows a CMOS ISFET macromodel;

DETAILED DESCRIPTION OF EMBODIMENTS

Figure 11:
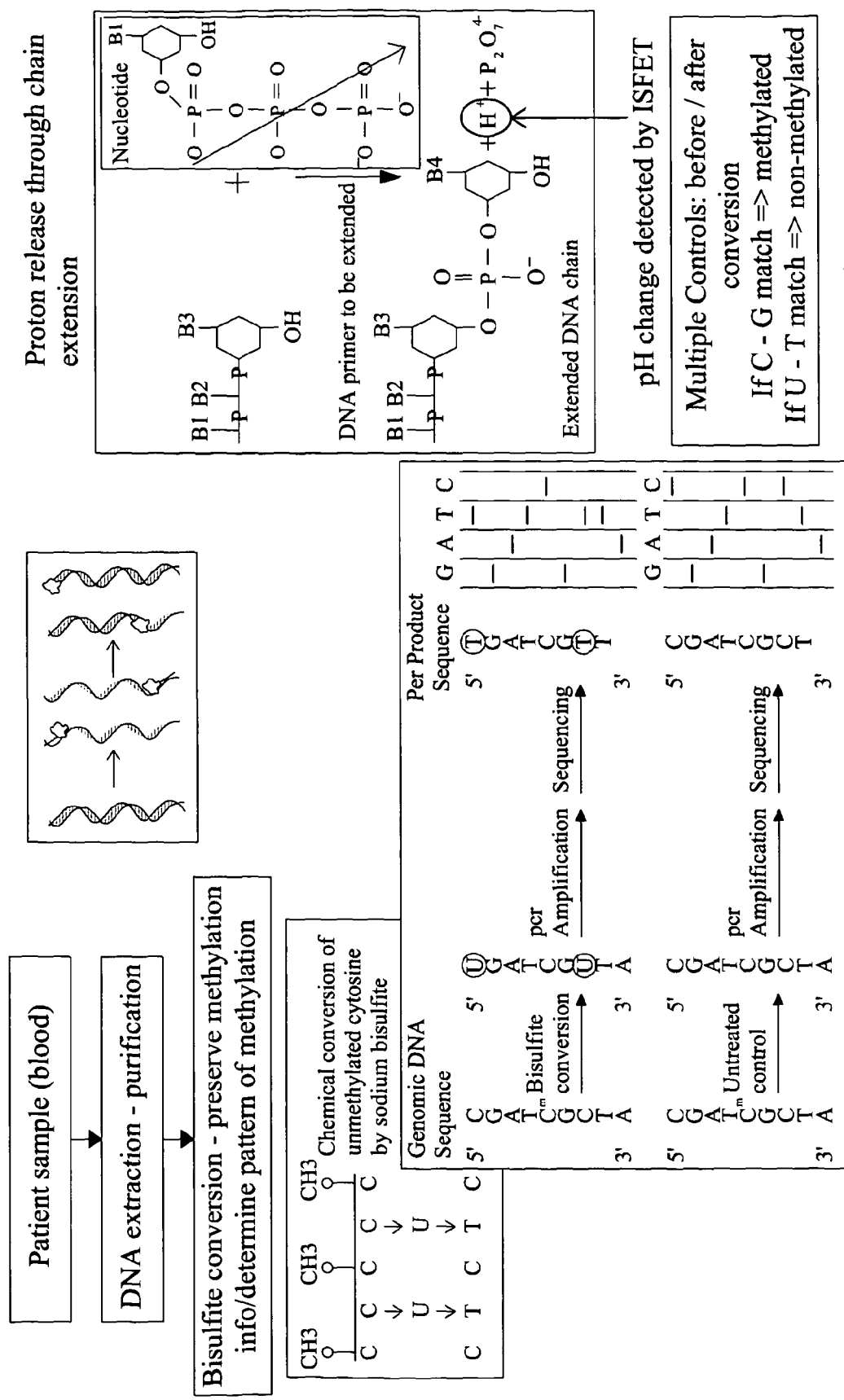
FIG. 11 shows schematically a method of an embodiment of the present invention.

In one embodiment, and with reference to FIG. 11
 A DNA sample to be tested is provided and purified and placed in a microfluidic chamber, bringing it in contact with the ISFET.
 A bisulphite treatment alters the DNA sample such that unmethylated cytosine locations become uracil.
 The treated sample is amplified using PCR. Uracil locations become thymine in the resulting DNA copies.
 The copies are denatured and a probe is hybridised up to the area of interest (for example, tumour promoter regions).
 Sequencing-by-synthesis is performed, adding different dNTP to the chamber one at a time. Hydrogen ions are released during the incorporation of a dNTP at the location to be determined. Guanine incorporates with the methylated cytosine, Adenine incorporates with both original thymine and thymine corresponding to uracil which corresponds to unmethylated cytosine. During each known dNTP addition, the electrical output signal of the ISFET is monitored.

In an alternative embodiment;
 A sample to be tested is provided and purified and placed in a microfluidic chamber bringing it in contact with the ISFET.
 A bisulfite treatment alters the sample such that unmethylated cytosine locations become uracil.
 The treated sample is amplified using PCR. Uracil locations become thymine in the resulting DNA copies.
 A probe, designed to have guanine in locations where the objective is to detect methylated cytosine, or adenine in locations where the objective is to detect unmethylated cytosine (uracil), is hybridises to denatured single stranded copies of the amplified DNA.
 Multiple dNTPs are added to the chamber together or one at a time. Hydrogen ions are released during the incorporation of multiple dNTPs at the 3' end of the probe, or chain extension. In the presence of a target sequence complimentary to the probe, chain extension and hydrogen ion release will occur, resulting in discrete fluctuations in the electrical output and signal of the ISFET. This may be compared with the absence of a target sequence complimentary to the probe. The electrical output signal of the ISFET is monitored after addition of dNTPs.

In yet another embodiment:

A sample to be tested is provided and purified and placed in a microfluidic chamber bringing it in contact with the ISFET and with apparatus for thermocycling of the chamber.

A bisulfite treatment alters the sample such that unmethylated cytosine locations become uracil.

A set of amplification primers, designed to have guanine in locations where the objective is to detect methylated cytosine (uracil), or adenine in locations where the objective is to detect unmethylated cytosine (uracil), are added to the chamber, along with amplification reagents, a polymerase enzyme and an excess of dNTPs.

The sample is thermocycled to perform PCR, and the electrical output signal of the ISFET is monitored as the thermocycling proceeds. Hydrogen ions are released during the incorporation of multiple dNTPs at the 3' end of the probe during the chain extension phase of PCR. In the presence of a target sequence complimentary to the probe, chain extension and hydrogen ion release will occur, resulting in discrete fluctuations in the electrical output signal of the ISFET. This may be compared with the absence of a target sequence complimentary to the probe. However, since the amplification mixture will buffer the release of hydrogen ions, amplification must proceed beyond a threshold number of cycles for buffering capacity of the sample to be overcome in order to generate an electrical output signal in response to a change in pH arising from chain extension during amplification in the presence of target DNA.

Any of the above embodiments may combine steps, or introduce reagents in a different order.

The time at which the fluctuations occur and the magnitude of the fluctuations is monitored to allow sequencing of DNA which in turn determines the location of methylated or unmethylated cytosine in the original sample. The electrical signal may be compared to a reference signal of a control chamber with a reference ISFET or to a reference electrode. A difference in the signal would indicate the incorporation versus non-incorporation of a known nucleotide at a location in the sequence.

The sequence of the treated sample may be compared with a control sequence or a previous sample to determine the quantity and location of methylated cytosine in the sample. For example the presence of a thymine instead of a cytosine (by the incorporation of a adenine instead of a guanine, respectively) might indicate that the original sample contained a non-methylated cytosine at a specific location.

The methylation of the sample DNA occurring in regions known to be promoters of messenger RNA and may affect the expression of the DNA.

The amount of DNA that is methylated and the percent of methylation of the original DNA in the sample will affect the magnitude of the signal output from the ISFET. This signal provides both an indication of the amount of methylation and where it is occurring which provides, for example a prediction of the probability of a tumour being present.

The method may be used with or without thermocycling. For example, thermocycling may be used to facilitate optimisation, using a sequencing enzyme such as taq polymerase or recombinant T7 polymerase. Where T7 polymerase is used, this may provide increased speed and improved accuracy of monitoring nucleotide insertion. The pH of the reagent mixture may be adjusted for example. A decrease of the pH will lead to the production of more hydrogen ions, but will also tend to kill off the reaction. Trials have shown pH 6.8 to be a useful value of pH. Magnesium will be added to the reagent mixture to actuate the enzyme. The concentrations of the reagents may be modified.

A typical thermocycling sequence is set out in table 1.

TABLE 1

Cycle Sequencing

| Temperature | Duration | Function |
|---|---|---|
| 95° C. | 30 sec | Denaturing of DNA template |
| 55° C. | 30 sec | Annealing of primer |
| 72° C. | 60 sec | DNA extension and termination |

Operating within a thermal cycler enables multiple repetition of the sequencing process with minimal manipulation. This allows signal to noise boosting and easier delineation of difficult to read regions such as GC rich regions or areas of single nucleotide repeats.

Figure 1B:
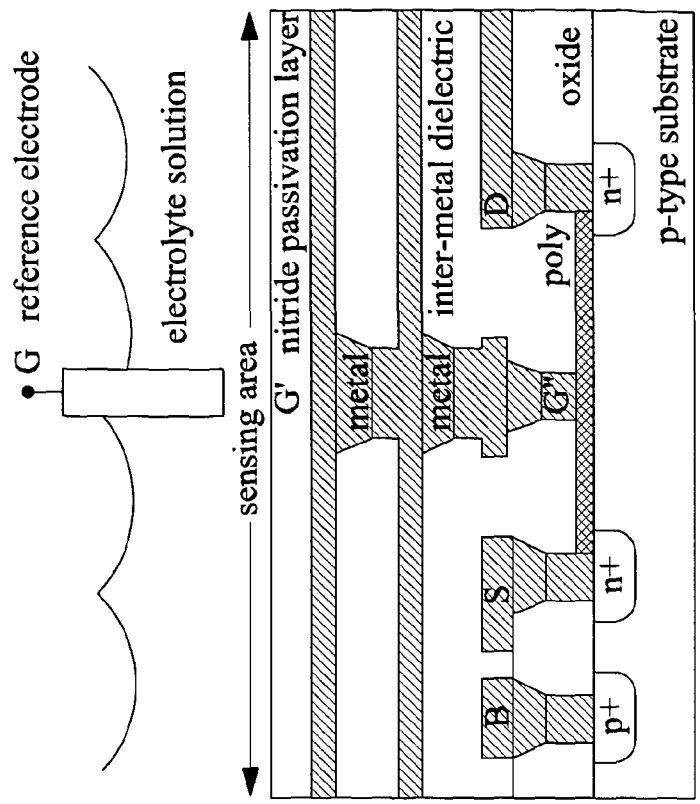
FIG. 1 is illustrates a sample solution exposed to a a) traditional ISFET arrangement and b) a floating gate ISFET.
Figure 1A:
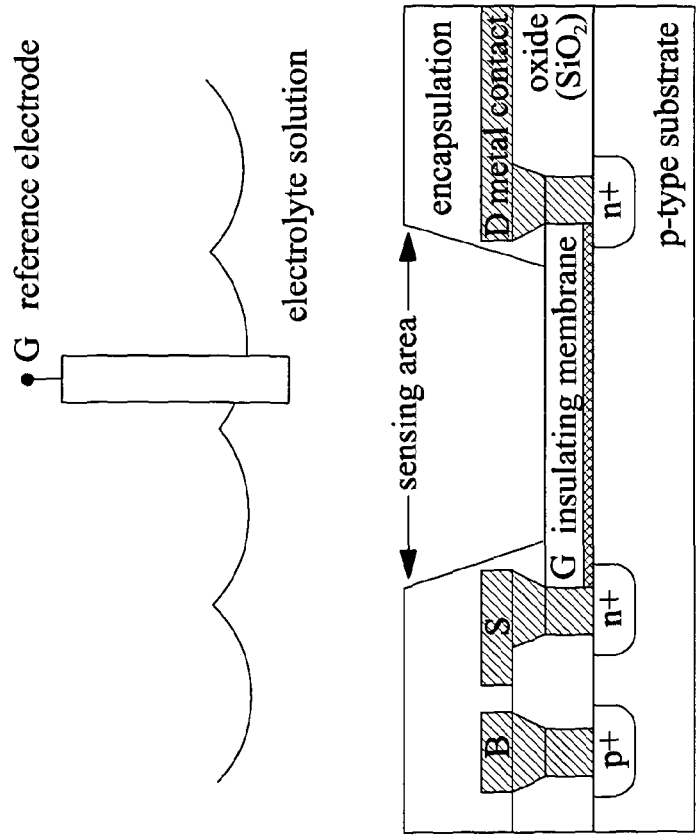

The ISFET is based on a MOSFET structure of a source and drain region, with a remote gate provided by an reference electrode exposed to an electrolyte solution in contact with a chemically-sensitive insulator capacitively coupled to the channel of the underlying device. Though sometimes described as such, the definition of the ISFET is not restricted to a structure without a metal gate as shown in FIG. 1a. More generally, an ISFET is defined as any FET with an ion-sensitive gate structure whose threshold voltage is modulated by changes in ion concentration. The ion sensitive gate structure can be composed purely of inorganic or organic insulating membranes as shown in FIG. 1a, or of a stacked gate structure comprising an electrically floating polysilicon gate connected to one or more metal layers covered by an ion-sensitive insulating membrane.

In a preferred embodiment, the pH-sensitive ISFETs with a silicon nitride insulating layer are fabricated in a standard CMOS process according to this latter stacked gate structure. This is an established technique reported extensively in the literature [1-4], which has the advantage of mass-manufacturability in standard semiconductor foundries without the need for either a modified process flow, additional mask steps or any post-processing steps. CMOS-based pH-ISFET structures use the passivation layer, commonly silicon nitride or silicon oxynitride, as the insulating layer in contact with the electrolyte solution whose pH is to be measured, and a floating gate stack of one or several metal layers available in a given CMOS process, connected between the polysilicon gate of an underlying field effect transistor and the passivation layer (FIG. 1b).

Figure 3:
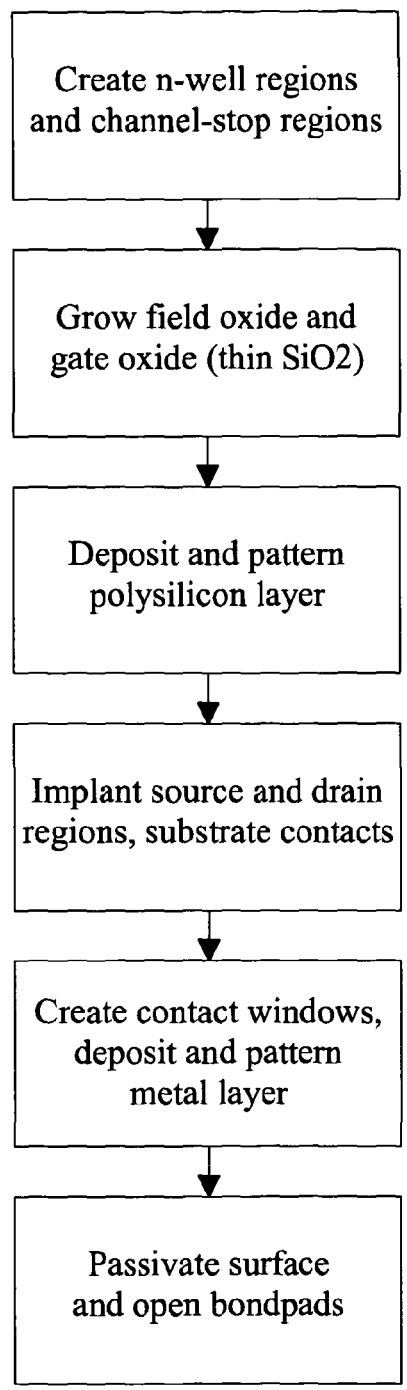
FIG. 3 shows a typical process flow in a commercial CMOS technology.

Any voltage applied to the reference electrode is capacitively-coupled via the electrolyte to the insulator surface, where a pH-dependent charge from ions on this interface modulates the channel current. This causes the observed shifts in the ISFET ID-VGS transfer characteristic, which can be represented as a modulation of its threshold voltage (Vth). In a CMOS ISFET pH-dependent charge which accumulates on the passivation surface is capacitively coupled to the floating gate structure beneath it, which in turn couples capicitively across the gate oxide to the channel between the source and drain terminals of the underlying field effect transistor. Thus, when the ISFET is biased by a reference electrode (typically Ag/AgCI or a Pt pseudo-electrode in differential applications), changes in ionic concentration at the insulator surface modulate the electrical output of the ISFET. The standard processing steps of a CMOS foundry (FIG. 3) can be used.

Any voltage applied to the reference electrode is capacitively-coupled via the electrolyte to the insulator surface, where a pH-dependent charge from ions on this interface modulates the channel current. This causes the observed shifts in the ISFET transfer characteristic, which can be represented as a modulation of its threshold voltage Vth. If the threshold voltage of the ISFET is defined with reference to its remote gate (G), the reference electrode, then it can be expressed as a combination of the intrinsic MOSFET threshold voltage of the device which belies it and the potential between the reference electrode and the top metal layer in contact with the polysilicon gate (FIG. 2b)

$$V_{th(ISFET)} = V_{th(MOSFET)} + V_{chem} \quad (1)$$

$$V_{chem} = \gamma + 2.3\alpha U_T \text{pH} \quad (2)$$

Where gamma is a grouping of all pH-independent chemical potentials and UT is the thermal voltage kT/q or RT/F as described in [5]

And in more detail, $$V_{th(MOSFET)} = \phi_{ma} + 2\phi_f - (Q_{ss} + Q_{sc})/C_{oz} \quad (3)$$

And $$V_{chem} = E_{ref} + \phi_{ij} + \chi_{eo} - \phi_{eo} - \frac{\phi_m}{q} \quad (4)$$

where the conventional MOSFET parameters are: the difference in metal-semiconductor work function $\phi_{ma}$, the Fermi potential of the semiconductor $\phi_f$, the fixed surface state charge density $Q_{ss}$, the semiconductor surface charge density $Q_{sc}$, and the insulator capacitance per unit area $C_{oz}$.

Vchem is a grouping of potentials of which $\phi_{eo}$ is the only pH-dependent term. $E_{ref}$ is the absolute electrode potential of a silver/silver chloride reference electrode relative to a vacuum, which can be found by adding 4.44V to the standard electrode potential normalised to the standard hydrogen electrode [99], $\phi_{ij}$ is the liquid junction potential difference between the reference solution and the electrolyte, $\phi_{eo}$ is the potential of the electrolyte-insulator interface, $\chi_{eo}$ is the electrolyte-insulator dipole potential, and $\phi_m/q$ is the metal work function which is included in $V_{chem}$ to be subtracted from $V_{th(MOSFET)}$ because there is no metal on the gate of the ISFET.

The dependence of the electrolyte-insulator interface potential ψeo on pH is modelled using a combination of the site-binding theory and the Gouy-Chapman-Stern double layer model.

The methylated DNA is processed using biology-based methods (using Bisulfite conversion and methylation-specific primer extension), the circuit defines the $I_{ref}$ and compares the $I_{out}$ with that via a translinear cell.

Figure 12:
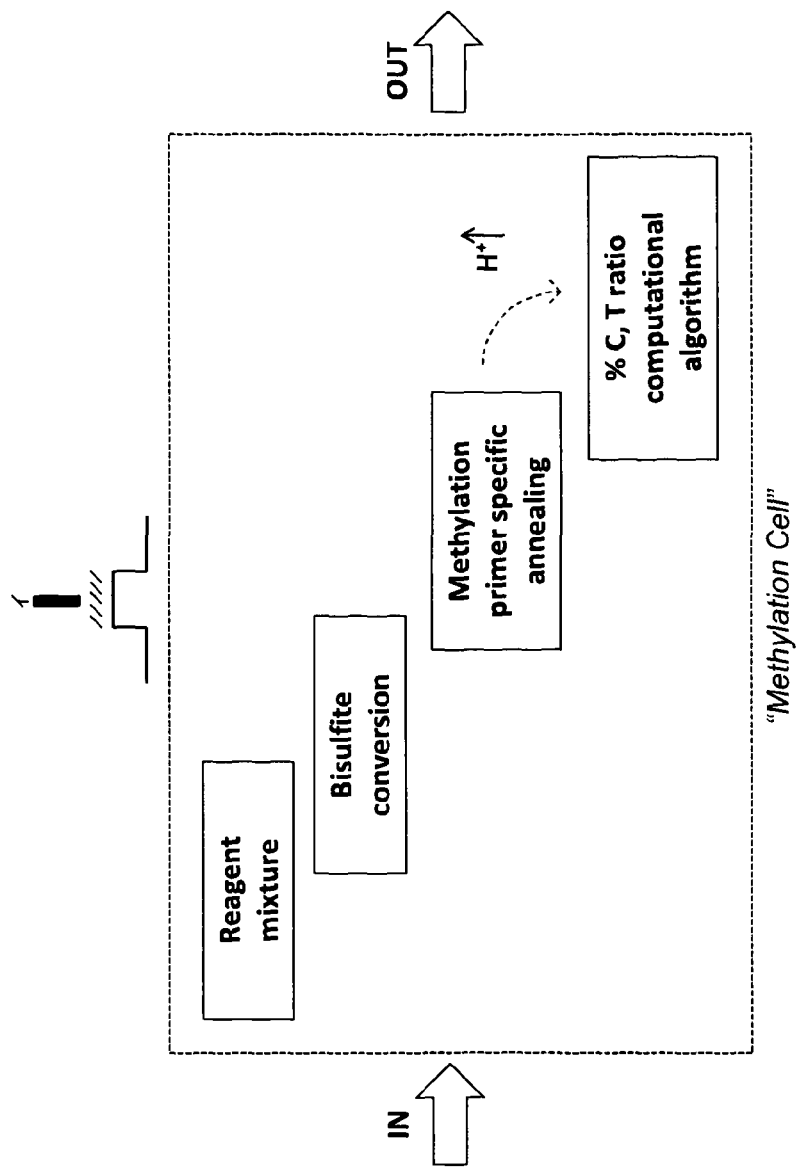
FIG. 12 shows a schematic of a methylation cell in accordance with an embodiment of the present invention.

The system, herein called a "Methylation Cell" (FIG. 12), could work in a real-time continuous way, utilising intelligent sensor design due to the integrative capability of ISFETs with standard circuit techniques. In more detail, the chemical front-end of the system, comprisesf: a) the reagent mixture, referring to either a DNA sequence comprising one or more CpG dinucleotides or a sequence treated with bisulfite reagents, as a means to discriminate the methylated from the unmethylated sequences of one or more CpGs and b) the process of methylation specific annealing using primer pairs so that hybridisation reaction occurs only with a target complementary region of the DNA sample through a hydrolysis reaction, dependent on the pH of the reaction.

Furthermore, the information obtained from the chemical part of the platform system will be analyzed by an electrical part through an ISFET-based sensor front-end implementation. Such interaction will determine a ratiometric signal as an output of the ISFET based sensors, acquired in a pH form, obtained from the prepared DNA samples, giving us a ratio between the methylated/unmethylated information, therefore determining the differences between a pathogenic gene and a normally methylated one. Such ratio will be obtained based upon the proportion of methylated aliquots presented above a pre-defined threshold value. Analysis of the ratio acquired will have the potential to enable the early detection of cancer with an improved accuracy coming from the intelligent processing algorithms when ISFETs are included.

Figure 13:
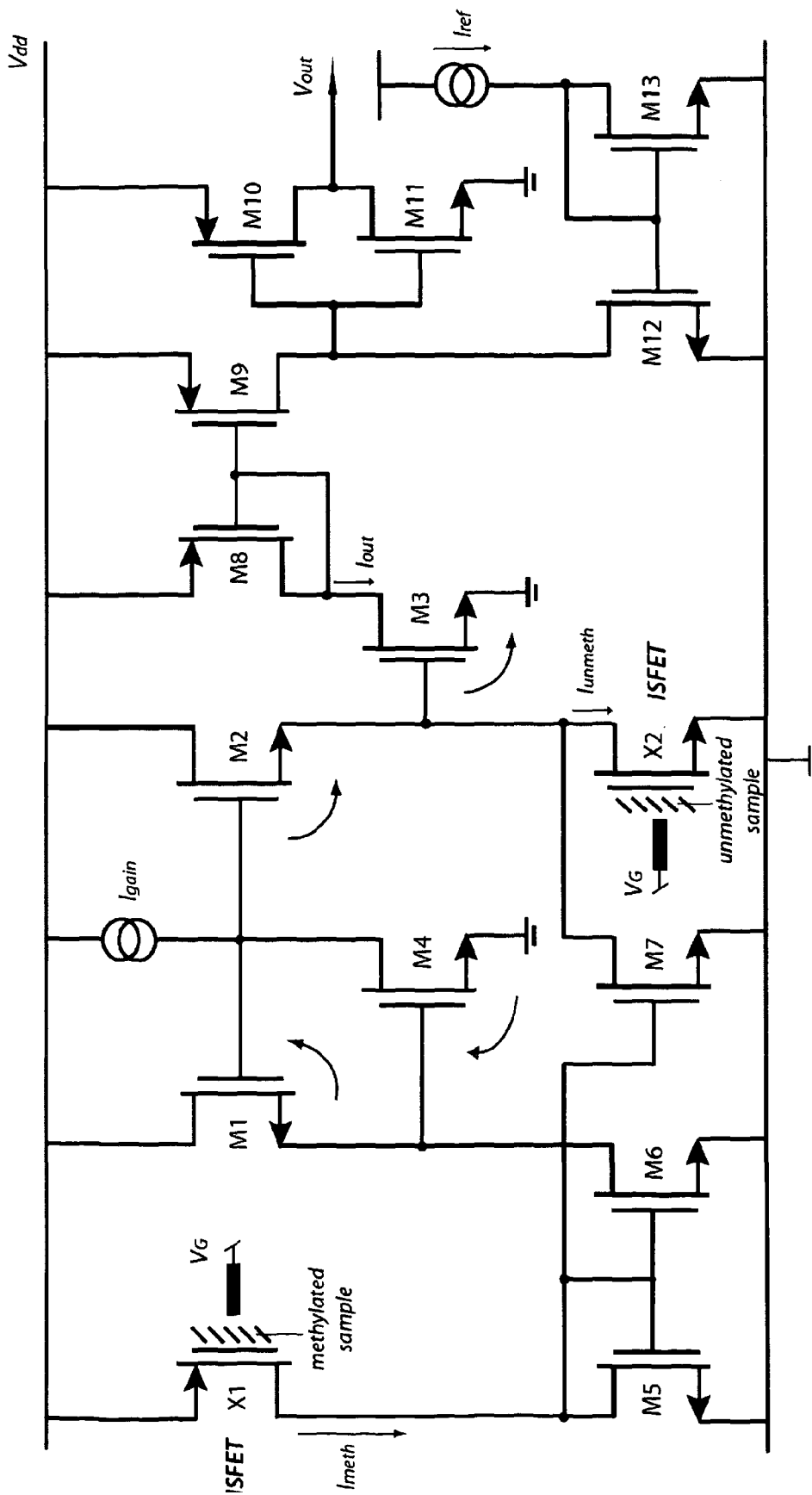
FIG. 13 shows an circuit incorporating ISFETs to provide an output signal in accordance with an embodiment of the present invention.

An integrated circuit is shown in FIG. 13, integrating two ISFETs to provide an output signal representative of the relative methylation in the patient sample versus a reference sample. The circuit may be covered with a microfluidic arrangement to provide wells above each ISFET and channels to deliver the sample and/or reagents. Reagents mix with the sample to produce hydrogen ions depending on the amount of methylation in the sample.

A sample is exposed to an ISFET sensor, X1, to test for evidence of aberrant methylation of a specific gene promoter (such as CDKN2A/p16-INK4, RASSF1, DAP kinase, H-cadherin, APC and O ^6-MGMT). The circuit 1 defines a reference current (Iref) and compares the output current (Iout) with that of the reference current through a current comparator consisting two current mirrors (M8-M9, M12-M13) and a CMOS inverter (M10, M11). A second ISFET sensor, X2, is exposed to a normally methylated sample (healthy control) labelled as the 'unmethylated sample'.

The circuit further comprises a translinear cell (MOSFETs M1, M2, M3, M4), capable of computing the division between the drain currents (Imeth and Iunmeth) given by the methylated, bisulfite converted DNA patient sample and the bisulfite converted unmethylated sample. For the current division, current mirrors are used (M5, M6, M7) so as to rotate the current's direction to fit into the translinear loop in a way such that the ratio of currents can be calculated using very few transistors.

Based on the comparison of the output current (Iout) with a reference (Iref), a CMOS inverter contributes in switching if the current is above a desired threshold set by Iref, therefore distinguishing the critical ratio values from the normal ones given particular CpG(s). The calculation of the methylation ratio derived from equation (4) is an indication of the level of aberrancy of methylation existent in a tumor suppressor genes of interest, over the overall methylation of the genes, therefore defining an epidemiological factor based on the disruption of the normality of the function of such genes correlated with the level of methylation accordingly.

The translinear cell capable of computing the division between drain currents given by the two ISFETs, X1 and X2, is shown. Translinear circuits exploit the exponential relationship between current and voltage in weak-inversion MOS transistors, used mostly to perform multiplication and division on current signals.

By performing a Kirchhoff Voltage Loop on the loop indicated by the errors we have:

$$V_{GS1}+V_{GS4}V_{GS2}+V_{GS3} \quad (2)$$

so after substituting for the weak-inversion drain current we end up having:

$$nU_t\ln\left(\frac{I_{meth}}{I_o}\right)+nU_t\ln\left(\frac{I_{gain}}{I_o}\right)=nU_t\ln\left(\frac{I_{meth}+I_{unmeth}}{I_o}\right)+nU_t\ln\left(\frac{I_{out}}{I_o}\right) \quad (3)$$

and by using the basic relation of adding natural logs we get the final expression for the ratio:

$$I_{out}=I_{gain}\frac{I_{meth}}{I_{meth}+I_{unmeth}} \quad (4)$$

whereby Igain is a pre-defined gain term on the ratio, Iout is the output current and both Imeth and Iunmeth are generalised drain currents (ID) of the ISFET devices X1 and X2, biased in weak inversion, defined as:

$$I_{D_{meth}}(X1)=I_o e^{\frac{V_{GS}}{nU_t}}K_{meth}[meth]^{\frac{a_{meth}}{n}} \quad (5)$$

$$I_{D_{unmeth}}(X2)=I_o e^{\frac{V_{GS}}{nU_t}}K_{unmeth}[unmeth]^{\frac{a_{unmeth}}{n}} \quad (6)$$

after substituting the values of interest in the equation:

$$I_D=I_o e^{\frac{V_{gs}}{nU_t}}K_{chem}[ionX]^{\frac{a_x}{n}} \quad (7)$$

whereby VGS is the gate source voltage of the device, Io is the intrinsic current, n is the weak-inversion slope coefficient, Ut is the thermal voltage, Kchem is a grouping of constant chemical potentials, αX is the sensitivity parameter and [ionX] is the concentration of ions in solution.

The above methylation cell can be scaled, exploiting the advantages of integration, scalability and low cost of implementation in unmodified CMOS technology to detect methylation in a plurality of genes. For example the methylation of gene 1 is exposed to X1 of circuit 1, whilst a healthy gene 1 is exposed to X2 of circuit 1. This is repeated until the Nth gene is exposed to sensors X1 and X2 of circuit N.

The amplified DNA sample is placed in several separate wells above a set of ISFETs X1. An amplified DNA standard is placed in several separate wells above a second set of ISFETs X2. Different probes designed to anneal at points before different CpG island of interest are separately added to each well. This compares the relative methylation of several genes of interest to a standard. The ratio of each Methylated gene is weighted according to which type of tumor is being examined to create an output diagnosis signal.

Figure 4:
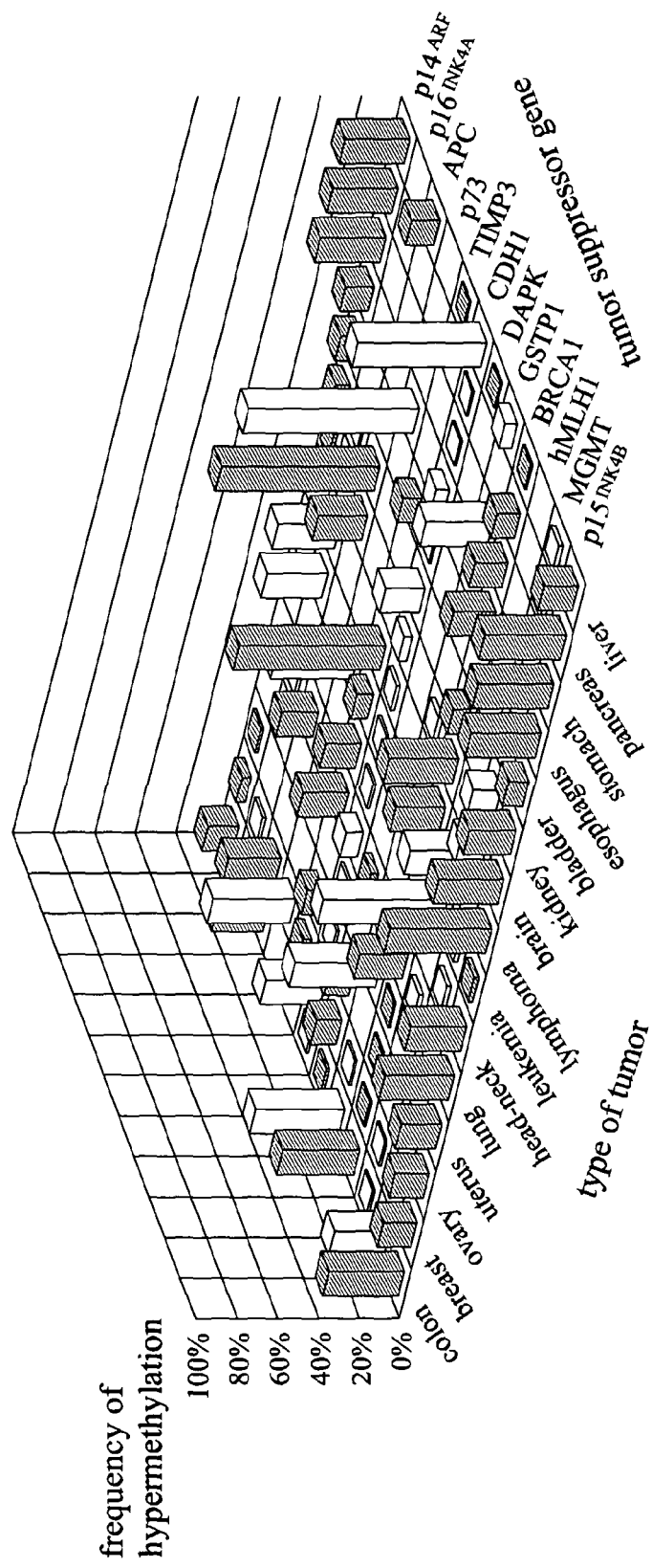
FIG. 4 is a 3-dimensional representation showing the relationship between frequency of hypermethylation, different tumour suppression genes and different tumour types.
Figure 5:
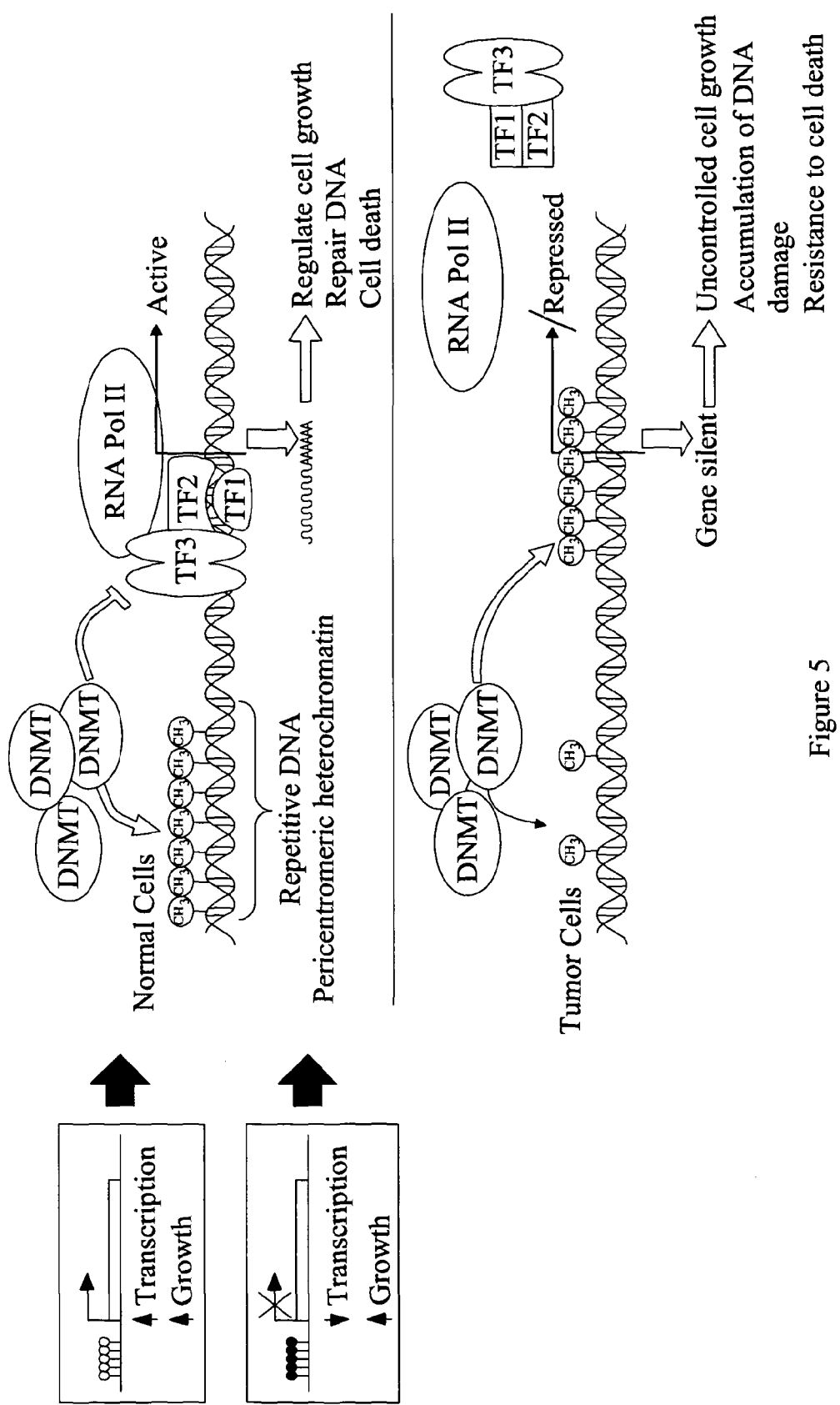
FIG. 5 shows the effect of methylation on transcription in normal cells and tumour cells.
Figures 6A, 6B:
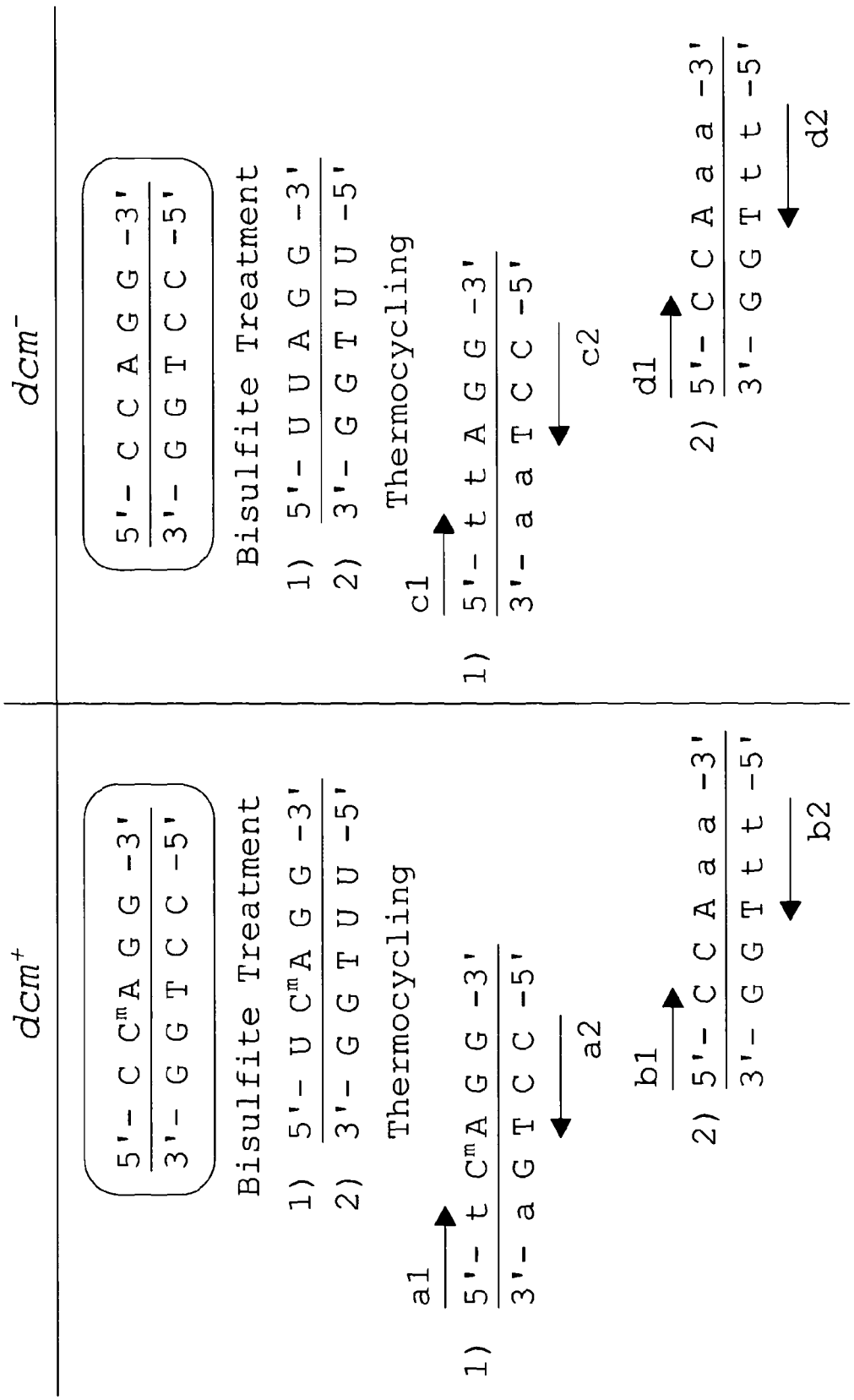
FIG. 6 exemplifies the changes to methylated and non-methylated DNA in a DNA sample subjected to bisulfite treatment followed by PCR, in accordance with an embodiment of the present invention.
Figure 7:
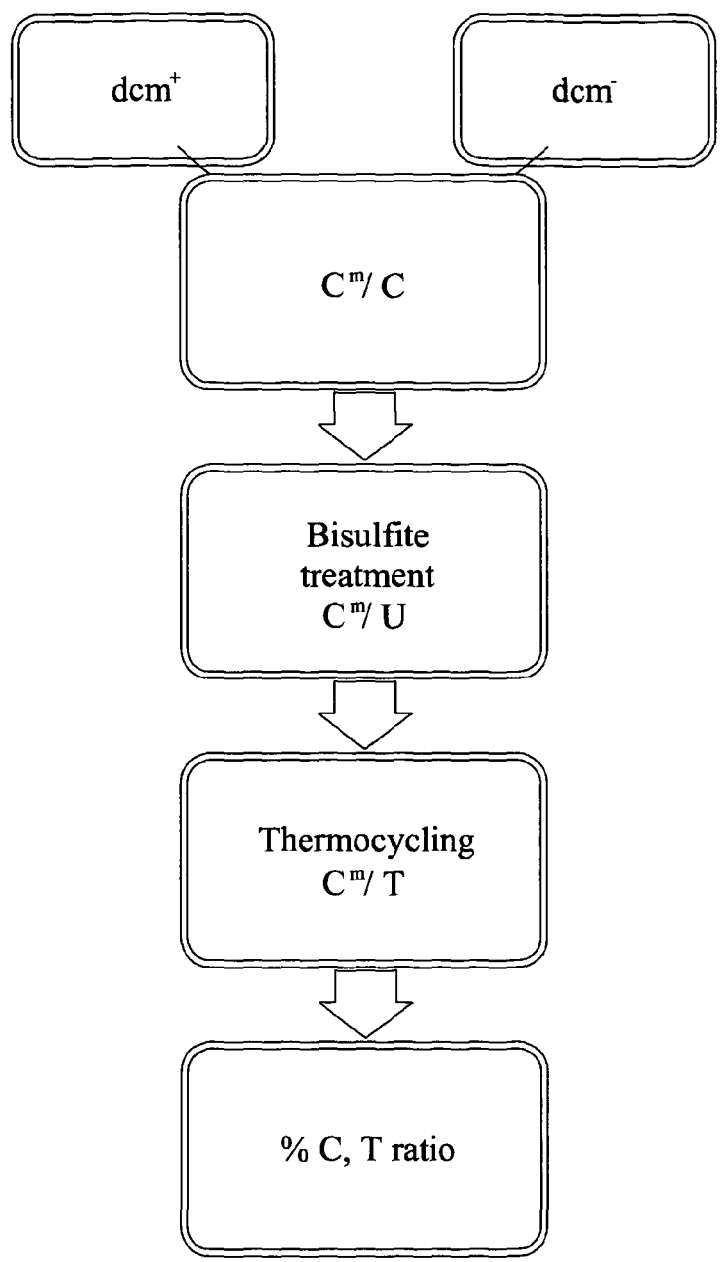
FIG. 7 shows the sequence of steps in determining metrics quantifying the methylation in a sample of DNA, in accordance with an embodiment of the present invention.
Figures 8A, 8B:
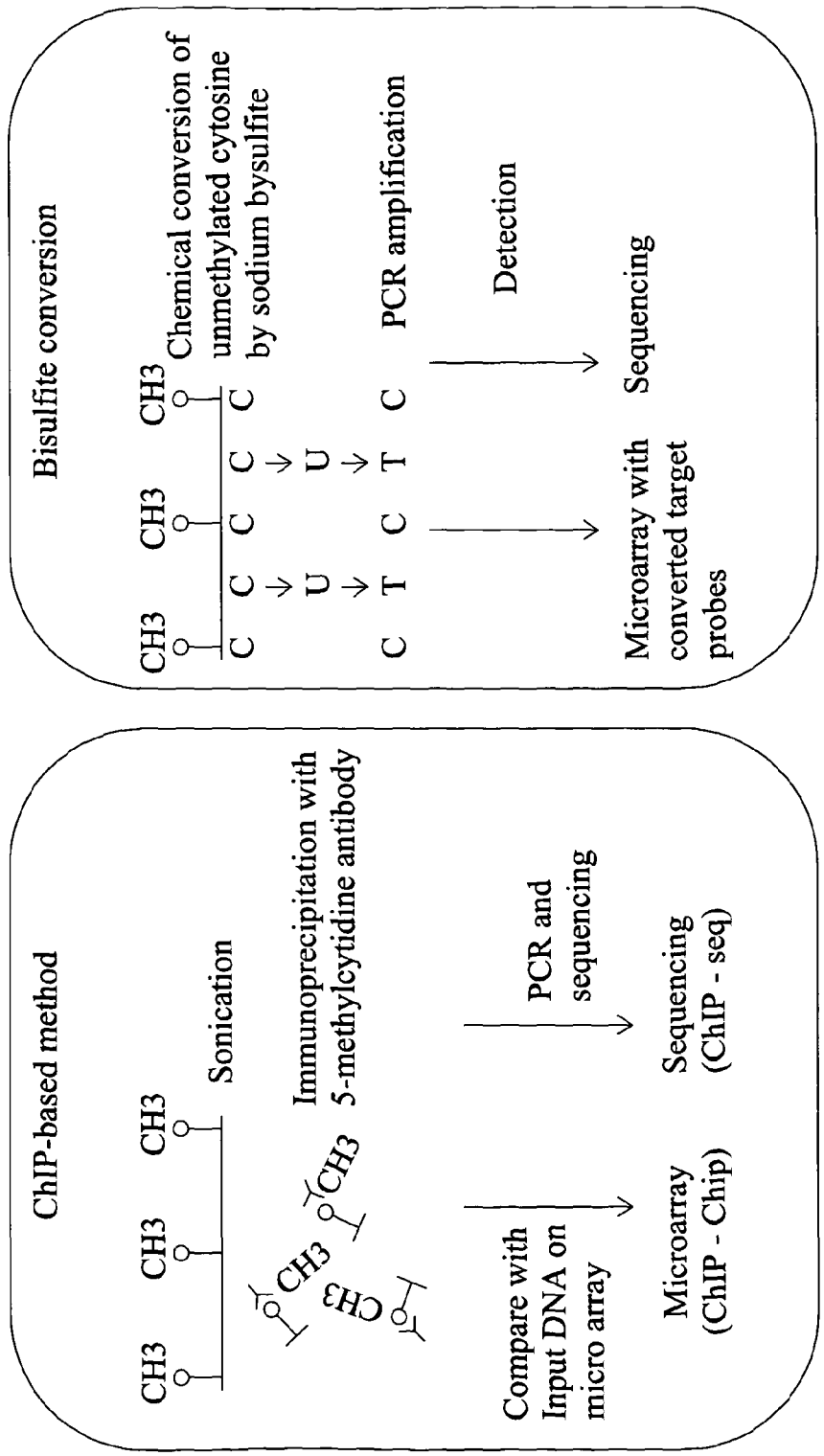
FIG. 8 shows schematically methods of methylation detection based on (a) immunoprecipitation and (b) bisulfite conversion.
Figure 9:
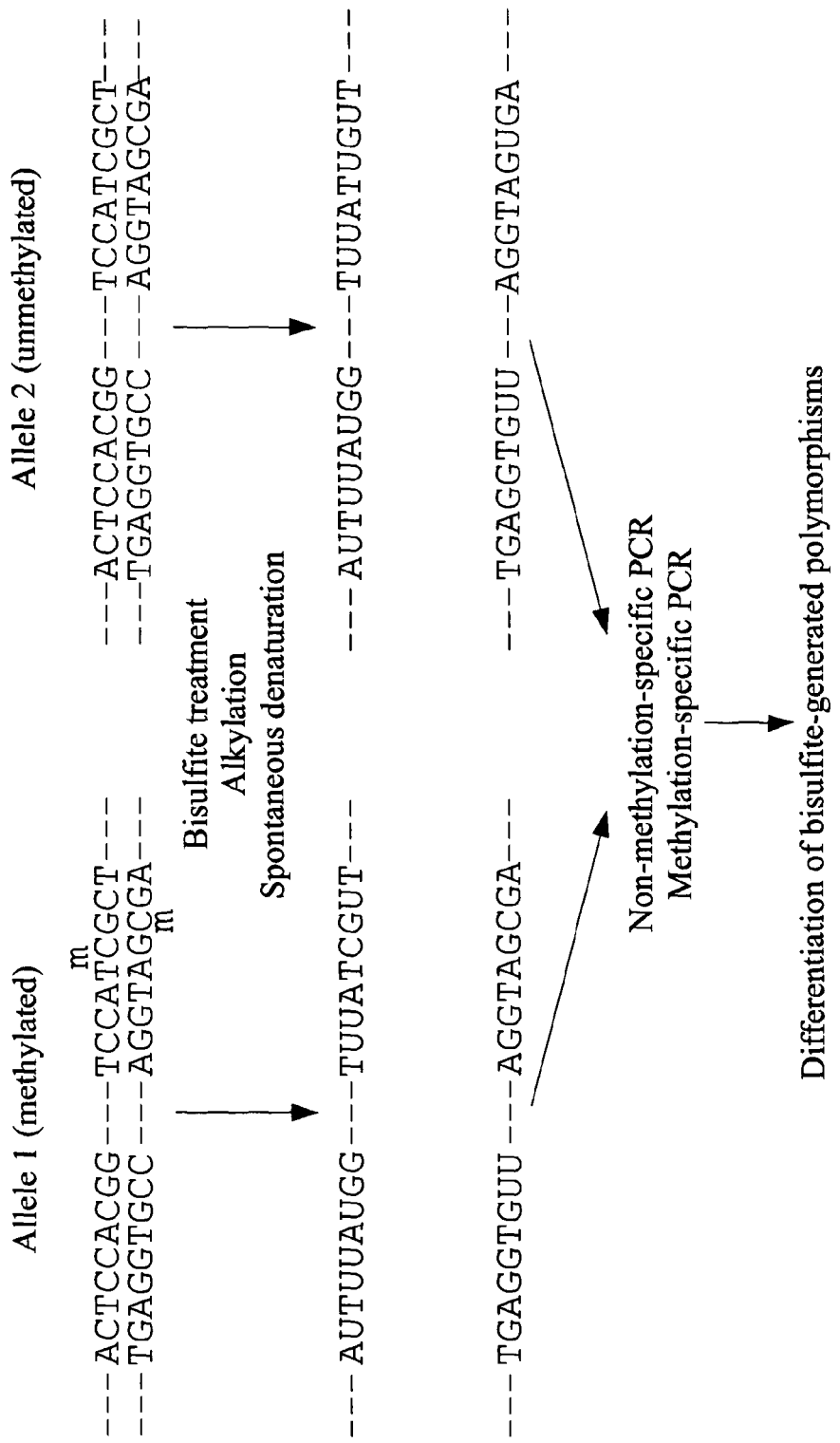
FIGS. 9 and 10 show the steps in a method for detecting DNA sequences using bisulfite treatment and known analytical methods.
Figure 10:
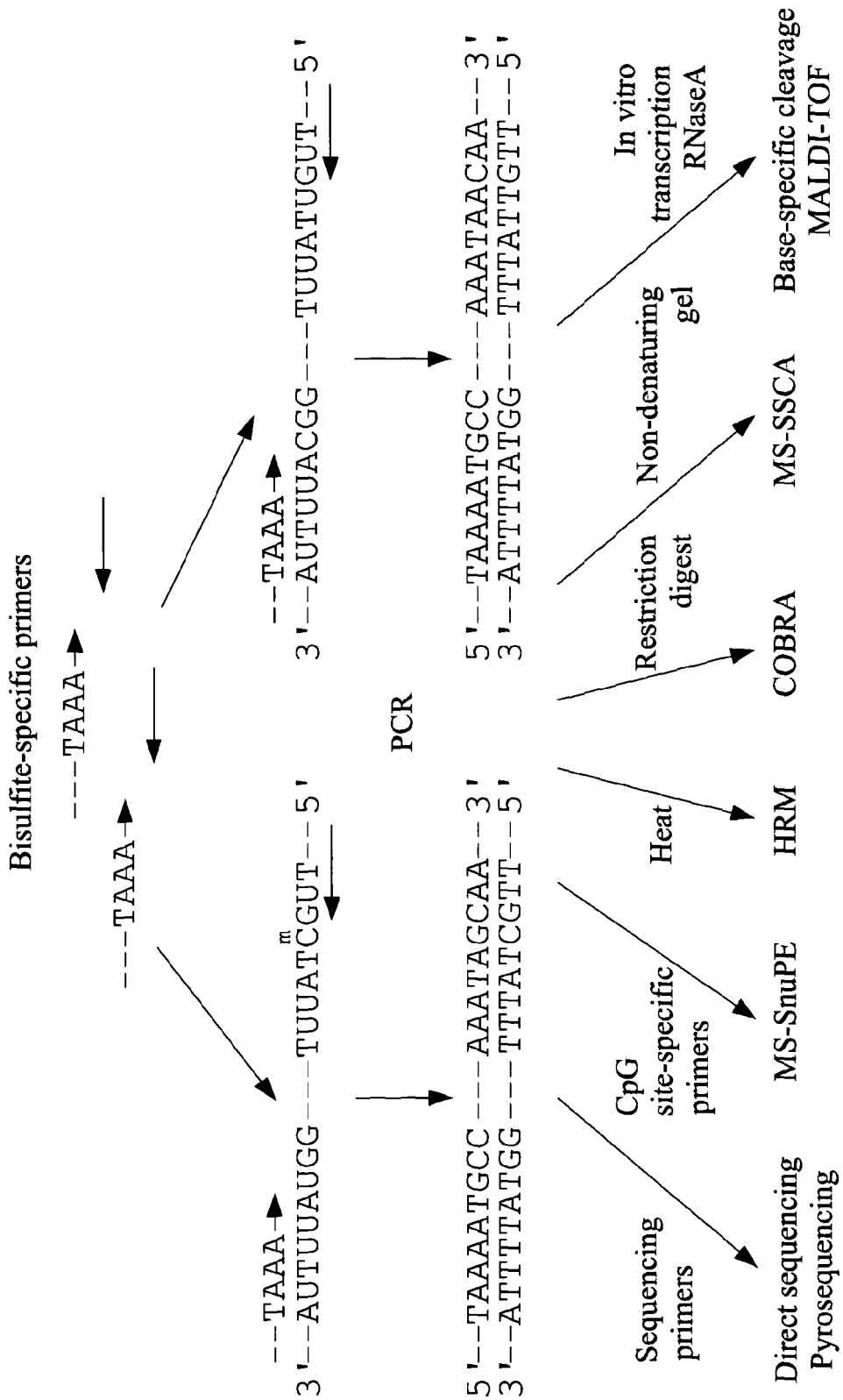

For example, studies have shown that detection of liver tumors are most highly correlated with the P15 (ink4b), CDH1, APC, and P14 (arf) tumor suppressor genes (see FIG. 4). Thus a complex indication of tumor likelihood could be based on the a weighted sum of the relevant methylation of these genes.

In one embodiment, multiple currents can be processed by adding ISFET sensors in parallel with X1, for example a plurality of sensors X1 providing a combined current Imeth. A plurality of unmethylated samples are exposed to a plurality of sensors in parallel with X2 providing a combined current Iunmeth.

Figure 14:
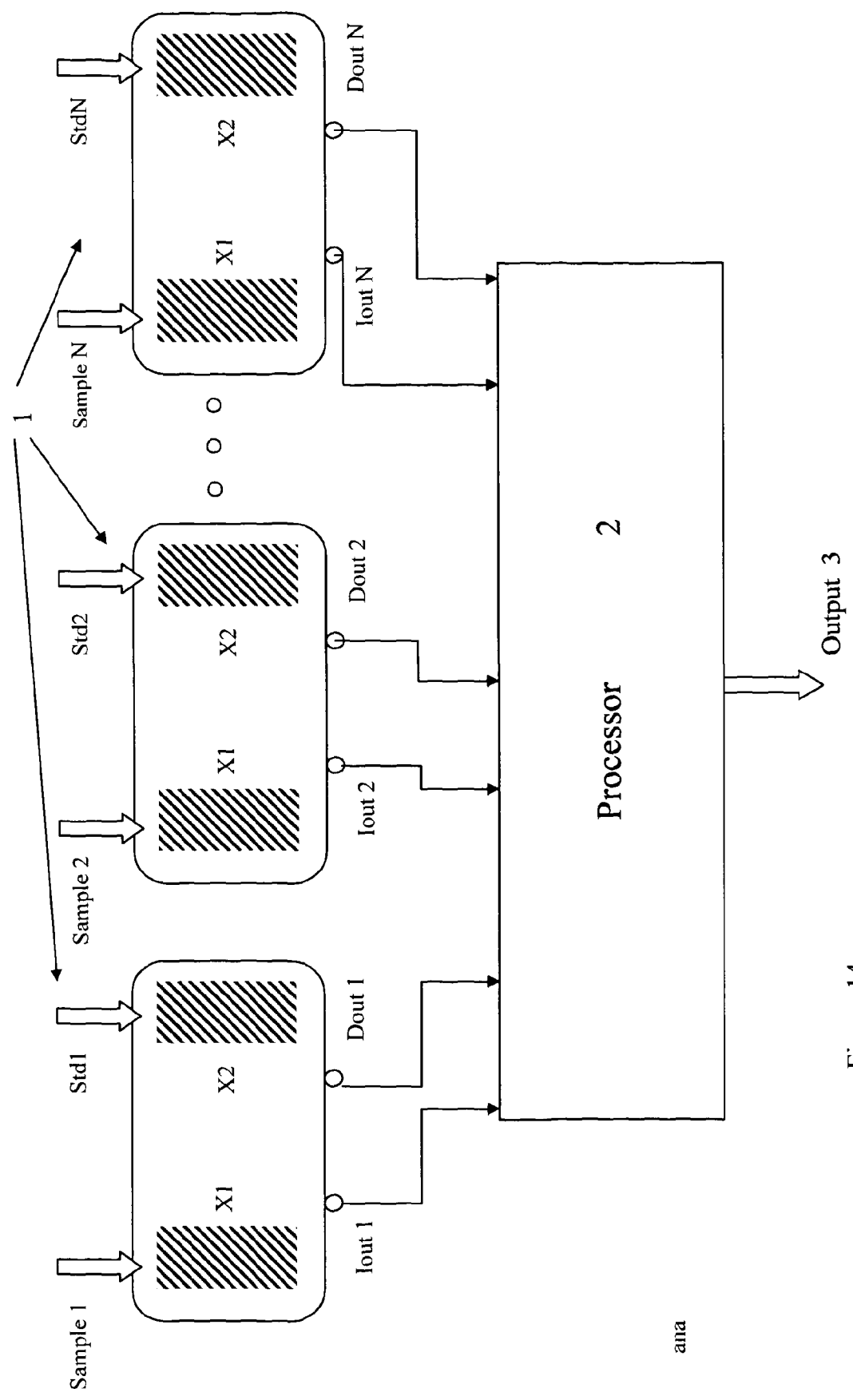
FIG. 14 shows a system circuit comprising a plurality of circuits such as that shown in FIG. 13 to provide an output signal.

In an alternative embodiment shown in FIG. 14, a plurality of circuits 1, each similar to that of FIG. 13, are connected to a processor 2 to provide an output signal 3. The processor may use the digital output of each circuit 1 (i.e. Vout) or the analogue signal representing the methylation ratio (i.e. Iout). The processor may be a computer or a circuit further integrated in CMOS with the sensor circuits 1.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. An apparatus for use in a method of detecting methylated nucleotides, comprising:
    (i) a first well, in which a first Ion Sensitive Field Effect Transistor (ISFET) having a floating gate arranged to monitor addition of one or more dNTPs to DNA strands during strand extension reactions when a first sample containing methylated DNA is brought into contact with the first ISFET when the first sample is loaded into the first well;
    (ii) a second well, in which a second ISFET having a floating gate arranged to monitor addition of one or more dNTPs to DNA strands during strand extension reactions when a second sample containing reference DNA is brought into contact with the second ISFET when the second sample is loaded into the second well; wherein the first well is separated from the second well;
    (iii) means for treating DNA in the first well and the second well of a microfluidic chamber with bisulfite which discriminates between methylated and non-methylated nucleotides;
    (iv) means for amplifying the treated DNA in the first well and the second well of a microfluidic chamber; and
    (v) a processor comprising a circuit, which is electrically coupled to an output of the first ISFET and an output of the second ISFET, wherein the circuit is arranged to provide an output signal of relative methylation, which output signal is derived from signals received from the first ISFET and the second ISFET.

2. The apparatus according to claim 1, wherein the first sample is compared to the second sample which contains unmethylated DNA.

3. The apparatus according to claim 1, wherein the first sample is compared to the second sample which contains a known amount of DNA methylation.

4. The apparatus according to claim 1, wherein the output signal is a ratio received from the signals of the first ISFET and the second ISFET.

5. The apparatus according to claim 1, further comprising a plurality of first ISFETs, each ISFET having a floating gate and exposable to samples looking at different methylation clusters.

6. The apparatus according to claim 1, wherein the first ISFET and the second ISFET are biased to operate in the weak inversion region.

7. The apparatus according to claim 1, wherein the first ISFET, the second ISFET, and the circuit are integrated on a substrate, transistors of the first ISFET and the second ISFET forming part of the circuit.

8. The apparatus according to claim 7, wherein the signals of the first ISFET and the second ISFET are electrical currents and the output signal of the circuit is a ratio of the electrical currents.

9. The apparatus according to claim 1, wherein the output signal is compared to a threshold signal to indicate a potential diagnostic or therapeutic outcome associated with a comparative methylation value at a site of interest.

10. The apparatus according to claim 1, further comprising a translinear cell for computing the division between drain currents of the first ISFET and the second ISFET, the cell comprising current mirrors for rotating the direction of the output of the first ISFET or the output of the second ISFET.

11. A method of detecting methylated nucleotides, comprising loading samples containing methylated DNA or reference DNA in the apparatus of claim 1.

12. The method according to claim 11, further comprising the initial step of subjecting the DNA sample to a process which breaks up the DNA into smaller fragments, prior to treatment with bisulfite.

13. The method according to claim 12, wherein the process is sonication.

14. The method according to claim 11, further comprising sequencing the amplified DNA.

15. The method according to claim 11, wherein amplification of the treated DNA is carried out using a PCR.

16. The method according to claim 15, wherein the PCR is carried out using methylation-specific primers which enable only treated DNA strands resulting from methylated DNA to be amplified.

17. The method according to claim 15, wherein the PCR is carried out using non-methylation-specific primers which enable only treated DNA strands resulting from unmethylated DNA to be amplified.

18. The method according to claim 11, wherein amplification of the treated DNA is carried out using methylation-specific or non-methylation specific primers.

19. The method according to claim 11, wherein a first ISFET having a floating gate is exposed to a first sample containing DNA; a second ISFET having a floating gate is exposed to a second sample containing DNA; and a circuit provides the output signal, which output signal is derived from signals of the first ISFET and the second ISFET.

* * * * *